US008289389B2

(12) United States Patent  (10) Patent No.: US 8,289,389 B2
Yoon et al.  (45) Date of Patent: Oct. 16, 2012

(54) VISUAL INSPECTOR FOR INSPECTING FLAT PANEL DISPLAY DEVICE AND VISUAL INSPECTING METHOD USING THE SAME

(75) Inventors: Kyeung Sic Yoon, Gumi-si (KR); Dong Hyon Nam, Seoul (KR)

(73) Assignee: LG Display Co., Ltd., Seoul (KR)

( * ) Notice: Subject to any disclaimer, the term of this patent is extended or adjusted under 35 U.S.C. 154(b) by 1393 days.

(21) Appl. No.: 11/474,354

(22) Filed: Jun. 26, 2006

(65) Prior Publication Data

US 2007/0159160 A1  Jul. 12, 2007

(30) Foreign Application Priority Data

Dec. 29, 2005 (KR) ........................ 10-2005-0133992

(51) Int. Cl.
*H04N 7/18* (2006.01)
(52) U.S. Cl. ....................................................... 348/131
(58) Field of Classification Search ................... 348/131
See application file for complete search history.

(56) References Cited

U.S. PATENT DOCUMENTS

| 6,362,884 B1 * | 3/2002 | Okahira et al. | ............... 356/399 |
| 2002/0187704 A1 * | 12/2002 | Monks | ............................. 445/3 |
| 2005/0167620 A1 * | 8/2005 | Cho et al. | ................. 250/559.45 |

FOREIGN PATENT DOCUMENTS

| JP | 2001-305075 | 10/2001 |
| KR | 10-2005-0087904 | 9/2005 |

* cited by examiner

*Primary Examiner* — Jay Patel
*Assistant Examiner* — Richard Torrente
(74) *Attorney, Agent, or Firm* — McKenna, Long, and Aldridge, LLP.

(57) ABSTRACT

A visual inspector for inspecting a flat panel display device and a visual inspecting method using the same are disclosed. The visual inspector includes an inspection unit including a base frame and a loading stage rotatably coupled to the base frame to load a display panel on a front side thereof and to transmit a light to the flat panel device; a reflective illumination unit installed in the upper space of the inspection unit to illuminate the display panel loaded on the front side of the loading stage; and a transparent illumination unit coupled to the rear side of the loading stage of the inspection unit to illuminate the display panel loaded on the front side of the loading stage.

7 Claims, 4 Drawing Sheets

VISUAL INSPECTOR FOR INSPECTING FLAT PANEL DISPLAY DEVICE AND VISUAL INSPECTING METHOD USING THE SAME

This application claims the benefit of Korean Patent Application No. 10-2005-133992, filed on Dec. 29, 2005, which is hereby incorporated by reference for all purposes as if fully set forth herein.

BACKGROUND OF THE INVENTION

1. Field of the Invention

The present invention relates to an apparatus for inspecting a display panel of a flat panel display device, and more particularly, to a visual inspector for inspecting a flat panel display device.

2. Discussion of the Related Art

Flat panel display devices are designed to be smaller in volume and lighter in weight than cathode ray tube display devices. Flat panel display devices include liquid crystal displays (LCDs), field emission displays (FEDs), plasma display panels (PDPs), and light emitting diode (LED) displays.

An apparatus of the related art is used to examine flat panel display devices to determine their quality. A light is projected onto the display panel (for example, an LCD panel) using the apparatus and a worker examines light reflected from the display panel to detect and evaluate defects in the display panel that will result in a low quality display during operation.

A visual inspector is an apparatus for performing a naked eye inspection of a display panel.

The visual inspector is designed to allow evaluating differences in light reflection at different illumination angles to determine whether the display panel is of inferior quality.

In a visual inspection process according to the related art, reflective illumination and transparent illumination are used to perform a reflective illumination inspection and a transparent illumination inspection, respectively.

The visual inspector of the related art includes an illumination structure (hereinafter referred to as a "reflective illumination unit") for providing reflective illumination and another illumination structure (hereinafter referred to a "transparent illumination unit") for providing transparent illumination, respectively.

In a visual inspection method of the related art, the transparent illumination unit is positioned at a predetermined distance (inspection distance) from a place where the inspection is carried out (hereinafter referred to as an "inspection unit") during the transparent illumination inspection.

During the reflective illumination inspection of the related art, the display panel is inclined at an angle to the vertical direction. Accordingly, the transparent illumination unit may interfere with the inclined display panel if the transparent illumination unit is positioned near the inspection unit. To prevent this interference, the transparent illumination unit is moved away form the inspection unit by a predetermined distance when carrying out the reflective illumination inspection. The time during the movement of the transparent illumination is "dead time" or time during a visual inspection during which evaluation of the display panel cannot be performed.

Because of the need to accommodate movement of the transparent illumination unit to perform the reflective illumination inspection, the visual inspector of the related art has a large overall footprint. Moreover, moving the transparent illumination unit to carry out the reflective illumination inspection increases dead time by the time taken to complete the movement of the transparent illumination unit.

When inspecting large sized display panels, the inspection distance must be increased in proportion to the size of the display panel, which may further increase the overall footprint of the visual inspector of the related art.

Limitations in the luminance of the transparent illumination unit of the related art may limit the precision of the transparent illumination inspection, particularly when the inspection distance is large.

SUMMARY OF THE INVENTION

Accordingly, the present invention is directed to a visual inspector for inspecting a flat panel display device and a visual inspecting method using the same that substantially obviate one or more problems due to limitations and disadvantages of the related art.

An advantage of the present invention is to provide a visual inspector for inspecting a flat panel display device in which a footprint of the overall apparatus is minimized, the dead time is reduced, and limits on the luminance of a transparent illumination unit are overcome so that the transparent illumination quality inspection can be carried out precisely, and a visual inspecting method of the flat panel display device using the same.

Additional advantages and features of the invention will be set forth in the description which follows, and in part will be apparent from the description or may be learned from practice of the invention. The objectives and other advantages of the invention may be realized and attained by the structure particularly pointed out in the written description and claims hereof as well as the appended drawings.

To achieve these and other advantages and in accordance with the purpose of the invention, as embodied and broadly described herein, a visual inspector for inspecting a flat panel display device includes: an inspection unit including a base frame and a loading stage rotatably coupled to the base frame to load a display panel on a front side thereof and to transmit a light therethrough; a reflective illumination unit installed in the upper space of the inspection unit to illuminate the display panel loaded on the front side of the loading stage; and a transparent illumination unit coupled to the rear side of the loading stage of the inspection unit to illuminate the display panel loaded on the front side of the loading stage.

In another aspect of the present invention, a method for inspecting a flat panel display device using a visual inspector includes: providing a display panel to a front side of a loading stage; inclining the loading stage at a first predetermined angle; illuminating a front side of the display panel to inspect a quality of the display panel; inclining the loading stage at a second predetermined angle; and illuminating a rear side of the display panel to inspect the quality of the display panel.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention.

In the drawings.

DETAILED DESCRIPTION OF THE ILLUSTRATED EMBODIMENTS

Reference will now be made in detail to embodiments of the present invention, examples of which are illustrated in the accompanying drawings. Wherever possible, the same reference numbers will be used throughout the drawings to refer to the same or like parts.

Figure 1:
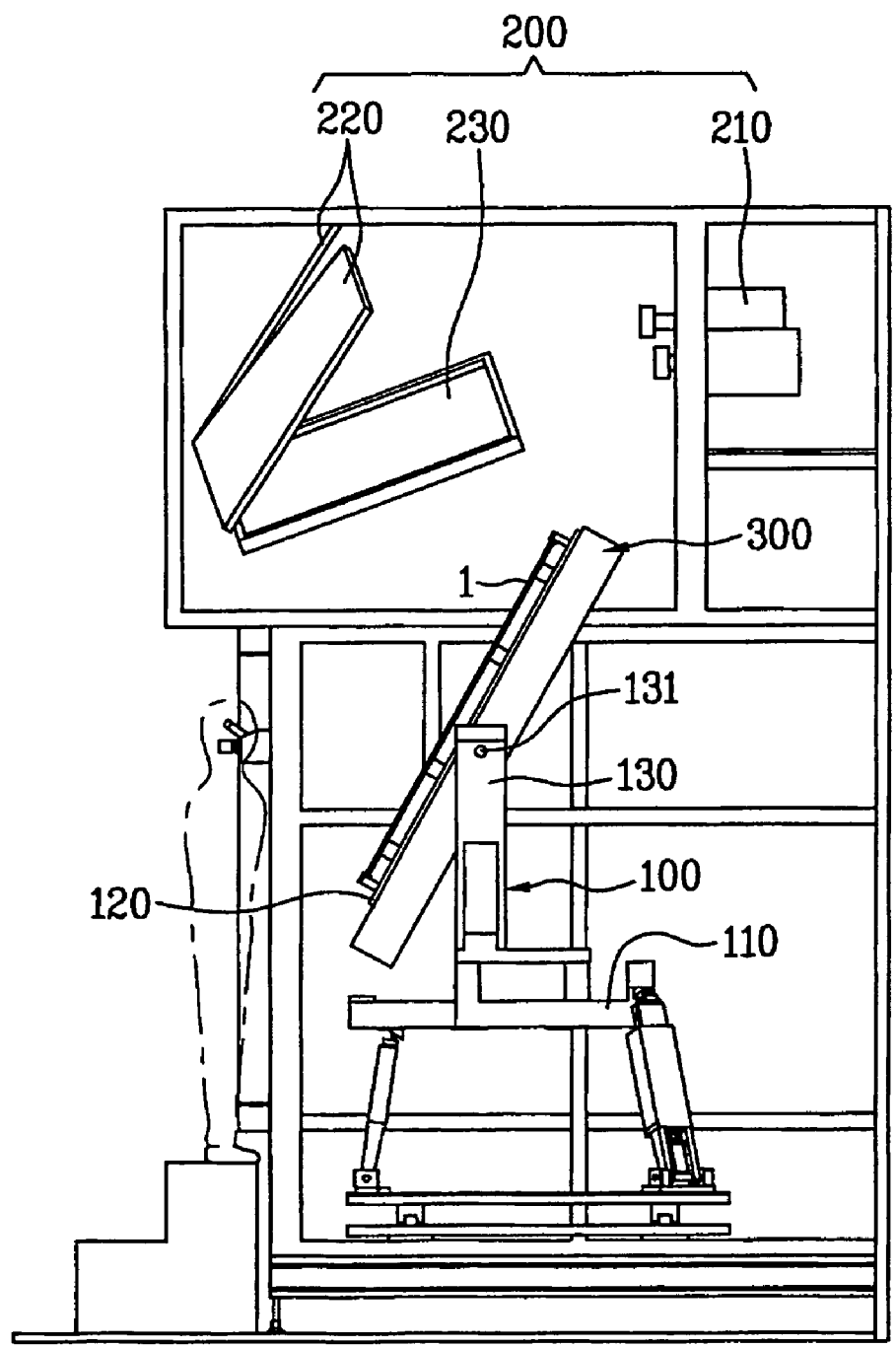
FIG. 1 is a side view schematically illustrating an internal structure of a visual inspector for inspecting a flat display device according to an embodiment of the present invention.

FIG. 1 schematically illustrates a visual inspector for inspecting a flat display device according to an embodiment of the present invention.

As shown in FIG. 1, a visual inspector for inspecting a flat panel display device includes an inspection unit 100, a reflective illumination unit 200, and a transparent illumination unit 300.

First, the inspection unit 100 will be described.

The inspection unit 100 is a device with which a worker inspects the quality of a display panel 1. For example, the display panel 1 may be an LCD panel.

The inspection unit 100 includes a base frame 110, a loading stage 120 and installation frames 130.

The base frame 110 is a part of a body of the inspection unit 100 and is structured to stand on a surface such as the ground. The base frame 110 can be movable, or can be fixed on a standing stage.

The installation frames 130 are coupled to both upper lateral sides of the base frame 110 to support the loading stage 120 and the transparent illumination unit 300. The loading stage 120 is rotatably coupled to the installation frames 130 at hinges 131 to rotate the loading stage 120 in the vertical direction. For example, the loading stage 120 may be indirectly rotatably coupled to the base frame 110 through the installation frames 130. In the indirectly coupled arrangement, the hinges 131 are directly coupled to respective sides of the installation frames 130. The hinges 131 are also directly rotatably coupled to the loading stage 120.

The loading stage 120 is structured to support and hold the display panel 1 on the front side thereof.

The loading stage 120 may be directly coupled to the respective installation frames 130 of the base frame 110 to rotate in the vertical direction at the hinges 131. That is, the hinges 131 may be directly rotatably coupled with intermediate portions of the respective lateral sides of the loading stage 120. Other arrangements for rotatably coupling the loading stage 120 to the base frame 110 to allow inclining the loading stage may be used.

Figure 2:
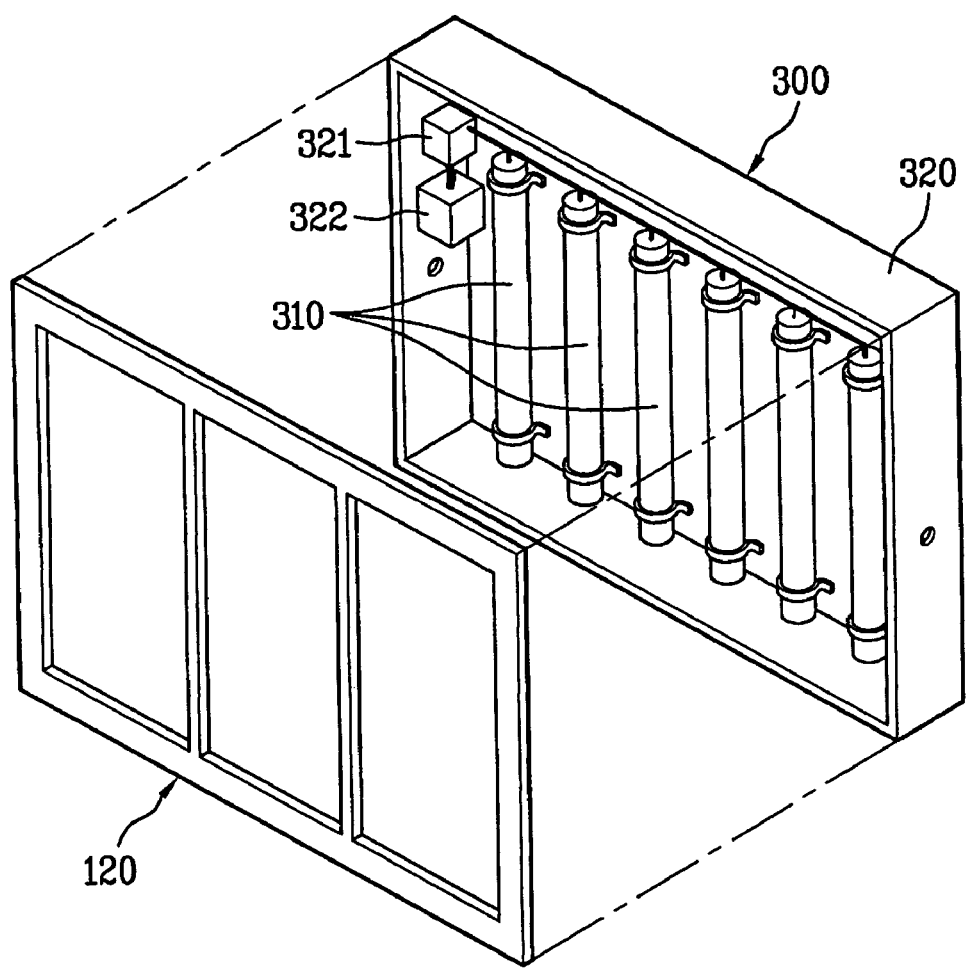
FIG. 2 is an exploded perspective view illustrating main parts of a loading frame and a transparent illumination unit of the visual inspector for inspecting a flat panel display device according to an embodiment of the present invention.

The overall loading stage 120 is made such that light can pass through the front surface of the loading stage 120. For example, the loading stage 120, as shown in FIG. 2, may be made in a lattice shape in which distances between the lattices are sufficiently wide to allow effective transmission of light to the rear side of the display panel 1.

Alternatively, the loading stage 120 may be formed of a material such as transparent acrylic or other material sufficiently transparent to allow transmission of light to the rear side of the display panel 1 for conducting an effective visual inspection.

Next, the reflective illumination unit 200 will be described with reference to FIG. 1.

The reflective illumination unit 200 is structured to illuminate the display panel 1 loaded on the front side of the loading stage 120.

The reflective illumination unit 200 is installed in the upper space of the inspection unit 100, and includes first illumination unit 210 and a reflective plate 220.

The first illumination unit 210 is a light source for providing a light and one, two, or more first illumination units 210 may be provided.

Moreover, the reflective plate 220 is a device for reflecting the light provided from the first illumination units 210 toward the display panel 1 loaded on the front side of the loading stage 120. One, two, or more reflective plates may be provided.

Moreover, the reflective illumination unit 200 may further include a polarizing plate 230.

The polarizing plate 230 is a device for polarizing the light reflected to the display panel 1 by the reflective plate 220 and is installed between the reflective plate 220 and the inspection unit 100. One, two, or more polarizing plates may be provided.

In the illustrated embodiment, the first illumination units 210 are installed at the rear upper sides of the inspection unit 100, and the reflective plates 220 are installed at the front upper sides of the inspection unit 100. Alternatively, other arrangements of the first illumination units 210 and the reflective plates 220 that allow light transmitted by the first illumination units 200 to be reflected towards the display panel 1 may be employed.

Next, the transparent illumination unit 300 will be described with reference to FIGS. 1 and 2.

The transparent illumination unit 300 is structured to illuminate the rear side of the display panel 1 loaded on the loading stage 120.

The transparent illumination unit 300 includes a second illumination unit 310 and a cabinet 320.

The second illumination unit 310 is a light source for illuminating the rear side of the display panel 1, and may include any one of a fluorescent lamp with internal electrodes such as a cold fluorescent lamp (CFL); a cold cathode fluorescent lamp (CCFL); an external electrode fluorescent lamp (EEFL) in which electrodes are provided outside of a tube; or a light emitting diode (LED).

Moreover, the cabinet 320 provides a space where the second illumination unit 310 is installed. The cabinet 300 may be made in the form of a box to be coupled to the rear side of the loading stage 120. In this configuration, the transparent illumination unit 300 can be rotated together with the loading stage 120.

The peripheral and the rear sides of the cabinet 320 may be made of a substantially opaque material, so that only the light provided from the second illumination unit 310 is provided to the display panel 1 through the rear side of the loading stage 120. When light is not transmitted through the peripheral and the rear sides of the cabinet 320, errors in the quality determination caused by an external light source (for example, a sidelight) can be essentially eliminated.

Moreover, the transparent illumination unit 300 further includes a controller 321 for controlling the second illumination unit 310 and a power supply 322. The controller 321 and the power supply 322 are installed in the cabinet 320.

Alternatively, the cabinet 320 of the transparent illumination unit 300 may be fixedly coupled to the rear side of the loading stage 120 and the lateral sides of the cabinet 320 may be coupled with the hinges 131 of the respective installation frames 130 of the inspection unit 100 to rotate thereby. In this case, the loading stage 120 is not coupled with the respective installation frames 130 but is fixed to the cabinet 320.

Hereinafter, a method of inspecting the display panel 1 with the naked eye using the visual inspector according to an embodiment of the present invention will be described with reference to the accompanying drawings, FIGS. 3 and 4, as follows.

First, the inspection using the reflective illumination (reflective illumination inspection) will be described.

For the reflective illumination inspection, the display panel 1 to be inspected is loaded on the front side of the loading stage 120.

Figure 3:
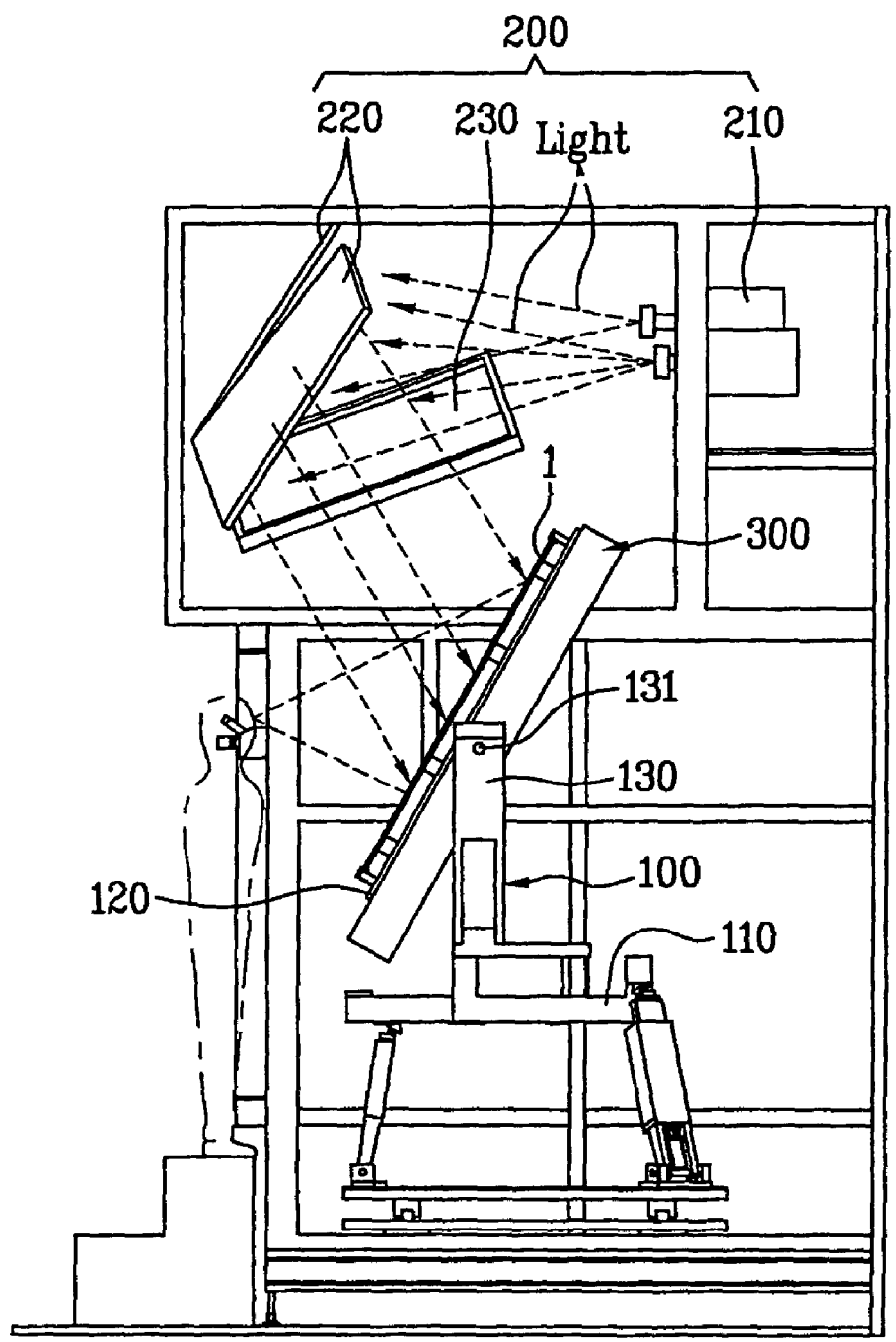
FIG. 3 is a side view illustrating a reflective illuminating examination procedure using the visual inspector for inspecting a flat panel display device according to an embodiment of the present invention.
Figure 4:
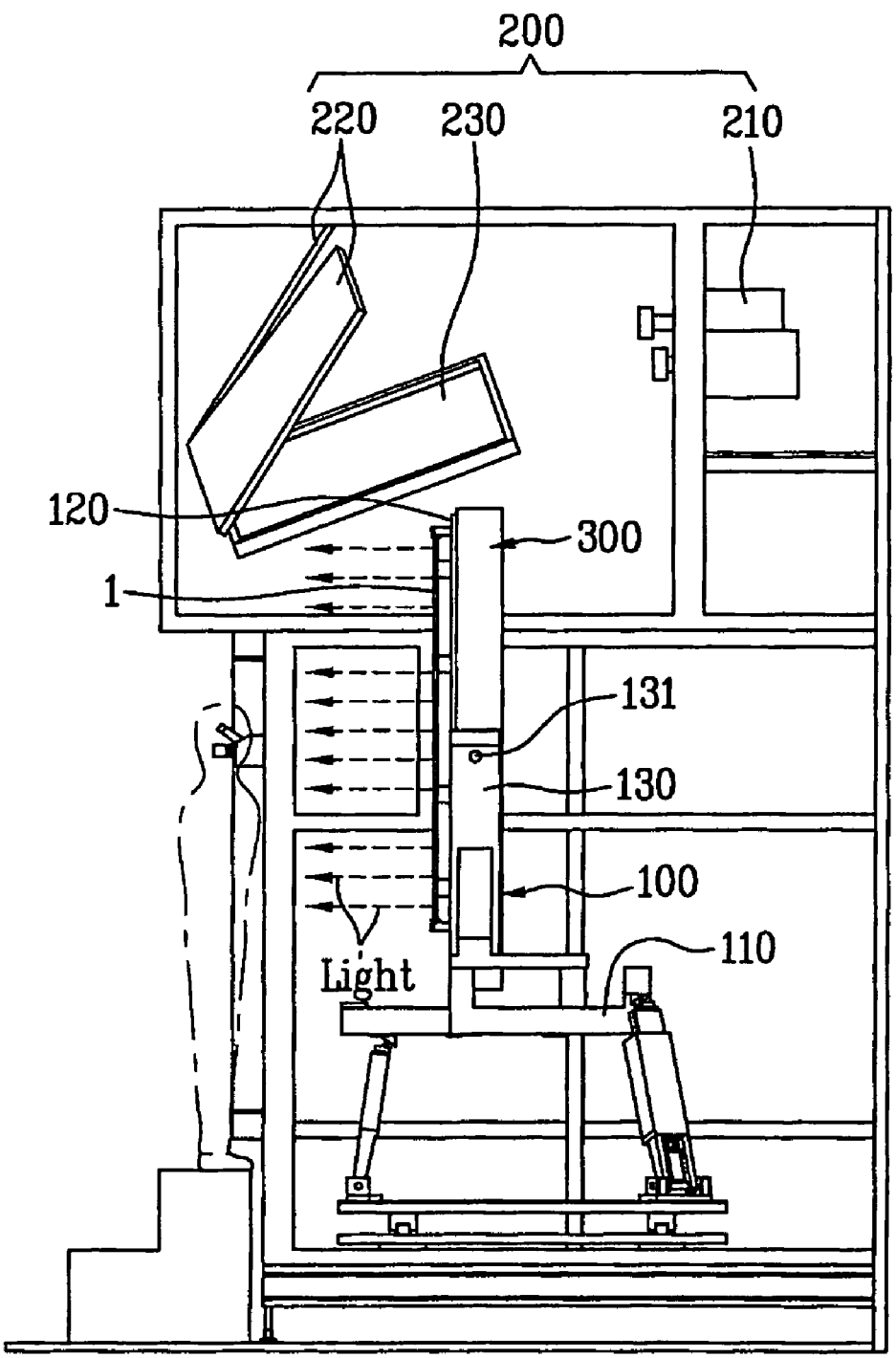
FIG. 4 is a side view illustrating a transparent illuminating examination procedure using the visual inspector for inspecting a flat panel display device according to an embodiment of the present invention.

During the reflective illumination inspection, the loading stage 120 is positioned such that the upper side thereof is inclined towards the rear of the inspection unit 100 about the hinges 131 as shown in FIG. 3.

The first illumination unit 210 of the reflective illumination unit 200 emits a light, and the second illumination unit 310 of the transparent illumination unit 300 is controlled not to emit light.

The light emitted from the first illumination unit 210 is reflected by the respective reflective plates 220 to the front side of the display panel 1. The reflected light may be polarized by the polarizing plate 230 located between the reflective plate 220 and the display panel 1.

A worker standing in front of the inspection unit 100 can view light reflected from the display panel 1 to visually inspect the display panel for normal regions, spots, and foreign matter.

An inspection using the transparent illumination (transparent illumination inspection) may be carried out after the reflective illumination inspection described above has been completed.

When conducting a transparent illumination inspection, the first illumination units 210 may be turned off so as not to emit light and the inclination of the loading stage 120 is adjusted to allow light from the second illumination unit 310 to be directed towards a worker. In the embodiment illustrated in FIG. 4, the loading stage 120 is inclined substantially vertically so that the front side of the loading stage 120 faces the worker. In other words, the loading stage 120 is inclined to an angle of about 90 degrees with respect to the ground.

During the transparent illumination inspection, the second illumination unit 310 of the transparent illumination unit 300 emits light to provide the illumination.

The emitted light from the second illumination unit 310 is provided to the rear side of the display panel 1 through the loading stage 120.

A worker standing in front of the inspection unit 100 can view the light transmitted through the display panel from the rear to the front side and can carry out the visual inspection of the display panel 1 for normal regions, spots, and foreign matter.

The reflective illumination inspection has been described above as being carried out before the transparent illumination inspection. Alternatively, the reflective illumination inspection may be carried out after the transparent illumination inspection or simultaneously with the transparent illumination inspection.

When the reflective illumination inspection is carried out simultaneously with the transparent illumination inspection, the first illumination units 210 may be turned on and the second illumination units 310 may be controlled to emit light so that light is provided to both the rear side and the front side of the display panel 1 loaded on the front side of the loading stage.

Using the above-described procedures may allow the quality inspection to be more precisely carried out and more widely applied then can be accomplished using the visual inspector of the related art.

As described above, integrally forming the inspection unit and the transparent illumination unit into a single body allows the footprint of the overall apparatus to be reduced.

Moreover, the distance between the display panel and the second illumination unit of the transparent illumination unit may be reduced so that the luminance limitation associated with the second illumination unit of the related art can be overcome allowing the quality inspection to be performed more precisely.

Further, eliminating need to change the position of the transparent illumination unit when carrying out the reflective inspection using the reflective illumination unit allows dead time to be reduced.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A visual inspector for inspecting a flat panel display device comprising: an inspection unit including a base frame and a loading stage indirectly and rotatably coupled to the base frame to load a display panel on a front side thereof and to transmit a light therethrough; a reflective illumination unit having a first light source and installed in the upper space of the inspection unit to illuminate the display panel loaded on the front side of the loading stage; and a transparent illumination unit having a second light source and coupled to the rear side of the loading stage of the inspection unit to illuminate the display panel loaded on the front side of the loading stage, the transparent illumination unit rotatable together with the loading stage at an angle of about 90 degrees so as to emit light from the second light source in a direction parallel with an upper surface of the base frame through the loading stage, wherein when conducting a transparent illumination inspection, the first light source is turned off so as not to emit light and the inclination of the loading stage is adjusted to allow light from the second light source to be directed towards a worker, wherein the inspection unit further includes installation frames coupled to the base frame, and center portions of both sides of the loading stage may be directly coupled to the respective installation frames to rotate in the vertical direction at hinges, and wherein the reflective illumination unit comprises a reflective plate for reflecting the light provided from the first light source to the display panel, and a polarizing plate for polarizing the light reflected by the reflective plate.

2. The visual inspector for inspecting a flat panel display device according to claim 1, wherein the loading stage is made of a transparent material.

3. The visual inspector for inspecting a flat panel display device according to claim 1, wherein the loading stage has a lattice shape.

4. The visual inspector for inspecting a flat panel display device according to claim 1, wherein the transparent illumination unit comprises:

a cabinet coupled with the rear side of the loading stage to provide a space where each of the at least one second light source is installed.

5. The visual inspector for inspecting a flat panel display device according to claim 4, wherein the at least one second light source comprises one of a fluorescent lamp with internal electrodes, a cold cathode fluorescent lamp (CCFL), an external electrode fluorescent lamp (EEFL), and a light emitting diode (LED).

6. The visual inspector for inspecting a flat panel display device according to claim 5, wherein peripheral and rear sides of the cabinet are made of materials through which a light cannot be transmitted.

7. The visual inspector for inspecting a flat panel display device according to claim 4, wherein the transparent illumination unit further comprises a controller to control the emitting of light of the at least one second light source.

* * * * *